US010155001B2

United States Patent
Sauzeau et al.

(10) Patent No.: US 10,155,001 B2
(45) Date of Patent: Dec. 18, 2018

(54) RAC1 INHIBITORS FOR INDUCING BRONCHODILATION

(71) Applicants: INSERM (Institut National de la Sante et de la Recherche Medicale), Paris (FR); Centre National de la Recherche Scientifique (CNRS), Paris (FR); Universite de Nantes, Nantes (FR); Centre Hospitalier Universitaire de Nantes, Nantes (FR)

(72) Inventors: Vincent Sauzeau, Nantes (FR); Gwennan Andre, Nantes (FR); Gervaise Loirand, Nantes (FR); Antoine Magnan, Nantes (FR); David Lair, Nantes (FR)

(73) Assignees: INSERM (Institut National de la Sante et de la Recherche Medicale), Paris (FR); Centre National de la Recherche Scientifique (CNRS), Paris (FR); Universite de Nantes, Nantes (FR); Centre Hospitalier Universitaire de Nantes, Nantes (FR)

( * ) Notice: Subject to any disclaimer, the term of this patent is extended or adjusted under 35 U.S.C. 154(b) by 0 days.

(21) Appl. No.: 14/897,970

(22) PCT Filed: Jun. 13, 2014

(86) PCT No.: PCT/EP2014/062402
§ 371 (c)(1),
(2) Date: Dec. 11, 2015

(87) PCT Pub. No.: WO2014/198909
PCT Pub. Date: Dec. 18, 2014

(65) Prior Publication Data
US 2016/0120872 A1   May 5, 2016

(30) Foreign Application Priority Data

Jun. 14, 2013 (EP) .................................. 13305808

(51) Int. Cl.
*A61K 31/5377* (2006.01)
*A61K 31/506* (2006.01)
*A61K 45/06* (2006.01)

(52) U.S. Cl.
CPC ........ *A61K 31/5377* (2013.01); *A61K 31/506* (2013.01); *A61K 45/06* (2013.01)

(58) Field of Classification Search
CPC ................ A61K 31/535; A61K 31/506; A61K 31/5377; A61K 45/06
USPC ...................................................... 514/235.2
See application file for complete search history.

(56) References Cited

U.S. PATENT DOCUMENTS

2013/0084275 A1   4/2013   Bokel et al.

FOREIGN PATENT DOCUMENTS

WO   2007016539 A2   2/2007

OTHER PUBLICATIONS

Papiris, Critical Care Feb. 2002, vol. 6, No. 1.*
J.S. Kim et al.; "8-oxo-2'-deoxyguanosine suppresses allergy-induced lung tissue remodeling in mice"; European Journal of Pharmacology, vol. 651, No. 1-3, Jan. 25, 2011, pp. 218-226.
Kuchar et al.; "Immunopathology of exercise-induced bronchoconstriction in athletes—A new modified inflamatory hypothesis"; Respiratory Physiology and Neurobiology, vol. 187, No. 1, Mar. 5, 2013, pp. 82-87.
Storck et al.; "Rho GTPases in pulmonary vascular dysfunction"; Vascular Pharmacology, vol. 58, No. 3, Mar. 2013, pp. 202-210.
Kim et al.; "TNF-alpha-induced up-regulation of intercellular adhesion molecule-1 is regulated by a Rac-ROS-dependent cascade in human airway epithelial cells"; Experimental & Molecular Medicine, vol. 40, No. 2, Apr. 2008, pp. 167-175.

* cited by examiner

*Primary Examiner* — Yong L Chu
(74) *Attorney, Agent, or Firm* — Whitham & Cook, P.C.

(57) ABSTRACT

The invention relates to a Rac1 inhibitor for use as bronchodilator in a patient in need thereof. The invention provides a Rac1 inhibitor for use in a method for inducing bronchodilation in a patient in need thereof. The invention also relates to a Rac1 inhibitor for use in a method for reducing AHR in a patient in need thereof.

4 Claims, 7 Drawing Sheets

RAC1 INHIBITORS FOR INDUCING BRONCHODILATION

FIELD OF THE INVENTION

The invention provides compounds and compositions for use as bronchodilator in a patient in need thereof. The invention provides compounds and compositions for use in a method for inducing bronchodilation in a patient in need thereof. The invention also provides compounds and compositions for use in a method reducing airway hyperresponsiveness in a patient in need thereof.

BACKGROUND OF THE INVENTION

Asthma is a heterogeneous inflammatory disorder of the airways characterized by chronic deregulated inflammation, bronchial hyperreactivity, and by symptoms of recurrent wheezing, coughing, and shortness of breath. Its prevalence has increased considerably over the past three decades, particularly in Western countries. Asthma is a major public health problem that affects 300 million people worldwide. Classically, the airway smooth muscle cells contribute to the pathogenesis of asthma mainly through its contractile properties: airway hyperresponsiveness (AHR), one of the main characteristics in asthma, refers to excessive contractile response of airway smooth muscle cells. The degree of AHR correlates with asthma severity and the need for therapy.

Regular treatment is composed by the inhalation of corticosteroids and long-acting beta2-adrenergic receptor agonists. However, severe asthma escapes to usual treatments or frequently requires higher doses. In acute asthma, two main classes of bronchodilators are available: short actin beta-2 agonists and anticholinergics. These drugs are rapidly effective in general. However in some cases as acute severe asthma they can be insufficient, so that new drugs acting through other pathways to reverse airways obstruction could help preventing the still elevated number of asthma deaths. The pathophysiology of asthma must therefore be better understood in order to identify new targets and design new treatments.

AHR is also observed in chronic obstructive pulmonary disease (COPD). COPD is characterized by airflow obstruction that is generally caused by chronic bronchitis, emphysema, or both. Commonly, the airway obstruction is incompletely reversible but most subjects do show a limited improvement in airway obstruction with treatment. In COPD, airway obstruction results from chronic and excessive secretion of abnormal airway mucus, inflammation, bronchospasm, and infection.

There is very little currently available treatment to alleviate symptoms of COPD, prevent exacerbations, preserve optimal lung function, and improve daily living activities and quality of life. Many subjects will use medication chronically for the rest of their lives, with the need for increased doses and additional drugs during exacerbations.

Thus, there is a need for additional treatment options in inducing bronchodilatation and managing airway hyperresponsiveness independently of airway inflammation in airway diseases, more particularly bronchoconstrictive disorders such as asthma or COPD.

SUMMARY OF THE INVENTION

In a first aspect, the invention relates to a Rac1 inhibitor for use in a method for inducing bronchodilation in a patient in need thereof.

In a second aspect, the invention relates to a pharmaceutical composition suitable for inhalation comprising a Rac1 inhibitor and a pharmaceutically acceptable carrier for use in a method for inducing bronchodilation in a patient in need thereof.

In a third aspect, the invention relates to a pharmaceutical composition or a kit-of-part composition comprising a Rac1 inhibitor and at least one additional therapeutic agent selected from the group consisting of anti-inflammatory drugs, β2-adrenergic receptor agonists, PDE3, PDE4, mixed PDE3/PDE4 and PDE5 inhibitors and muscarinic M3 antagonists.

DETAILED DESCRIPTION OF THE INVENTION

The invention is based on the discovery that administration of a Rac1 inhibitor is useful for inducing bronchodilation and preventing bronchospasm in mammals including humans independently of its inhibitory effect on inflammation, more particularly airway inflammation. As such Rac1 inhibitor may be administered to those prone to asthma and other conditions characterized by bronchoconstriction to relieve such constriction.

AHR is a sign of airway smooth muscle cells (aSMC) contraction, which may or may not be associated with underlying airway inflammation, leading to constricted airways and difficulties to breath. The inventors have addressed the contribution of Rac1 in the airway responses. Indeed mice having a smooth muscle-specific Rac1 deficiency (SM-Rac1-KO mice) displayed reduced metacholine-induced airway response in the OVA-sensitized model of allergic asthma. Same results have been obtained with distinct classes of Rac1 inhibitor, respectively NSC 23766 (an inhibitor of Rac1 activation) and EHT 1864 (an inhibitor of Rac1 activity). These observations highlighted Rac1 upstream of the cascade regulating AHR and showed that the Rac1 blockade as a potential therapeutic strategy for respiratory diseases including COPD and asthma.

Therapeutic Methods and Uses

Accordingly, the invention provides compounds and compositions (such as pharmaceutical compositions) for use as bronchodilator in a patient in need thereof The invention provides compounds and compositions for use in a method for inducing bronchodilation in a patient in need thereof. The invention also provides compounds and compositions for use in a method for preventing or reducing AHR in a patient in need thereof.

Accordingly, in a first aspect, the invention relates to a Rac1 inhibitor for use as bronchodilator in a patient in need thereof.

As used herein, the term "bronchodilator" refers to any compound that dilate the bronchi and bronchioles and by doing so decrease resistance in the respiratory airway and increase airflow to the lungs. They are useful in bronchoconstrictive disorder such as asthma in which an obstruction of airflow and bronchospasm is involved.

Bronchodilators are either short-acting or long-acting. Short-acting bronchodilators are used in "rescue" inhalers to provide rapid relief from acute bronchoconstriction. Medications such as salbutamol usually take effect within 20 minutes or less and provide temporary relief from asthma symptoms or flare-ups. Some short-acting β-agonists such as salbutamol are specific to the lungs and can relieve bronchospasms without unwanted cardiac (β1) side effects of non-specific β agonists such as ephedrine or epinephrine. Long-acting β2-agonists such as salmeterol and formoterol are useful for preventing bronchoconstriction but are not useful for fast relief Such medications can relieve airway constriction for up to 12 hours and can be taken twice a day with anti-inflammatory medications.

The invention also relates to a Rac1 inhibitor for use in a method for inducing bronchodilation (or for providing relief of bronchospasm) in a patient in need thereof As used herein, the term "bronchodilation" refers to the expansion of the bronchial air passages to treat or prevent a bronchoconstrictive disorder. As used herein, the term "bronchoconstrictive disorder" refers to any disorder or disease related to the reduction in the inner diameter of the bronchial pathway, e.g., a bronchus or bronchi, including, but not limited to, asthma, chronic obstructive pulmonary disease (COPD) and cystic fibrosis.

In one embodiment of the invention, the bronchoconstriction is not caused by airway inflammation.

In a second aspect, the invention relates to a Rac1 inhibitor for use in a method for reducing AHR in a patient in need thereof.

According to the invention, "airway hyperresponsiveness" or "AHR" refers to an abnormality of the airways that consists in an exaggerated airway-narrowing response to many environmental triggers, such as allergen and exercise. AHR can be a functional alteration of the respiratory system caused by inflammation or airway remodeling. AHR can be caused by collagen deposition, bronchospasm, airway smooth muscle hypertrophy, airway smooth muscle contraction, mucus secretion, cellular deposits, epithelial destruction, alteration of epithelial permeability, alterations of smooth muscle function or sensitivity, abnormalities of the lung parenchyma and/or infiltrative diseases in and around the airways. Many of these causative factors can be associated with inflammation. The invention is directed to any AHR, including AHR that is associated with inflammation of the airway (e.g. inflammatory cytokine production) as well as AHR that is not associated with inflammation of the airway.

In one embodiment of the invention, the AHR is not caused by airway inflammation.

As used herein, "reducing AHR" refers to any measurable reduction in AHR and/or any reduction of the occurrence or frequency with which AHR occurs in a subject. Preferably, AHR is reduced, optimally, to an extent that the subject no longer suffers discomfort and/or altered function resulting from or associated with AHR. A reduction in AHR can be measured using any suitable method known in the art. Respiratory function can be measured by spirometry completed by plethysmography, spontaneously or after inhalation of pharmacologic agents such as methacholine. It is also indirectly appreciated by peak flows, symptom scores, physical signs (i.e. respiratory rate), wheezing, exercise tolerance, use of rescue medication (i.e. bronchodilators) and blood gases.

Typically, the patient in need thereof suffers from a disease selected from the group consisting of asthma, chronic obstructive pulmonary, airways or lung disease (COPD, COAD or COLD), cystic fibrosis, and bronchiectasis and exacerbation of airways hyperreactivity.

Asthma is a complex disorder characterized by variable and recurring symptoms, reversible airflow obstruction (e.g., by bronchodilator) and bronchial hyperresponsiveness which may or may not be associated with underlying inflammation. Examples of asthma include pediatric asthma, bronchial asthma, allergic asthma, non-allergic (intrinsic) asthma, aspirine-sensitive asthma, occupational asthma, exercise-induced asthma, mild asthma, moderate to severe asthma, severe asthma, and steroid-resistant asthma.

In one embodiment of the invention, the patient in need thereof suffers from a disease (including asthma) in which airway inflammation is not involved. Typically, asthma attacks can be triggered by vigorous or prolonged exercise or physical exertion.

In one embodiment of the invention, the patient in need thereof is a patient with acute exacerbations of asthma.

In one embodiment of the invention, the patient in need thereof is a salbutamol-resistant patient.

As used herein, the term "Rac1" has its general meaning in the art and refers to ras-related C3 botulinum toxin substrate 1 (rho family, small GTP binding protein Rac1). Rac1 is a member of the Rho family of low molecular weight GTPases and are related to each other based on sequence homology and function (Vojtek, A. B., and Cooper, J. A., Cell 1995, 82, 527-529). In an active state, they bind to GTP and transduce signals of other proteins in signal transduction pathways. In their inactive state, they are bound to GDP. Members of the Rho family are typically involved in regulation of the actin cytoskeleton. The naturally occurring human Rac1 gene has a nucleotide sequence as shown in Genbank Accession number NM_006908.4 and the naturally occurring human Rac1 protein has an amino acid sequence of 192 amino acids as shown in GenBank database under accession number NP_008839.2

As used herein, the term "Rac1 inhibitor" designates any compound or treatment that reduces or blocks the activity of Rac1. More preferred Rac1 inhibitors are compounds that inhibit Rac1 activation by its GEFs (guanine nucleotide exchange factor) in an exchange assay, and/or that inhibit the activity of Rac1 (such as the activation of Pak1 by its phosphorylation as described in the section EXAMPLE below), and/or that inhibit the contractions of the airway smooth muscle cells (aSMC), and/or that inhibits the increase of intracellular $Ca^{2+}$ in aSMC. Rac1 inhibitors are well known in the art. The term "Rac1 inhibitor" also encompasses inhibitors of Rac-specific GEF family member, blocking thus specifically the Rac1 pathway. The term "Rac1 inhibitor" also includes inhibitors of Rac1 gene expression.

A typical example of Rac1 inhibitors includes NSC 23766 described in international patent application WO 2007/016539. The compound is a cell-permeable pyrimidine compound that specifically and reversibly inhibits Rac1 GDP/GTP exchange activity by interfering Rac1 interaction with Rac-specific GEFs.

Another typical example of Rac1 inhibitors includes EHT 1864 described in international patent application WO 2004/076445. EHT 1864 is a small molecule that blocks the Rac1 signaling pathways.

Other examples of Rac1 inhibitors include those described in EP2433636, WO2007031878, WO2007016539, WO2009007457 and WO2005051392.

Examples of Rac1 inhibitors which are activity inhibitors include Rac1 inhibitor W56, sold by Tocris Biosciences (Ellisville, Mo.) or the inhibitors described in Yuan Gao, et al. PNAS, May 18, 2004, vol. 101, 7618-7623.

Another example of Rac1 inhibitor is $N^4$-(9-Ethyl-9H-carbazol-3-yl)-N2-(3-morpholin-4-yl-propyl)-pyrimidine-2,4-diamine (also known as EHop-016) which is disclosed in Montalvo-Ortiz et al., Characterization of EHop-016 J Biol Chem. 2012 April 13;287(16):13228-13238 and US patent application No. US2013/172552.

In one embodiment, the Rac1 inhibitor is a selective Rac1 inhibitor. In the context of the invention, selective Rac1 inhibitors are compounds, which are preferably selective for the Rac1 GTPase as compared with the other Rac GTPase, such as Rac2 or Rac3.

Such selective inhibitors may be selected among inhibitors of Rac1 gene expression.

As used herein, the term "inhibitor of gene expression" refers to a natural or synthetic compound that has a biological effect to inhibit the expression of a gene.

In a preferred embodiment of the invention, said inhibitor of gene expression is a siRNA, a shRNA, an antisense oligonucleotide or a ribozyme.

Inhibitors of gene expression for use in the present invention may be based on antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein (i.e. Rac-1), and thus activity, in a cell. For example, antisense oligonucleotides of at least about 15 bases and complementary to unique regions of the mRNA transcript sequence encoding the target protein can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

shRNAs (short hairpin RNA) can also function as inhibitors of gene expression for use in the present invention.

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Antisense oligonucleotides, siRNAs, shRNAs and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER ("A Laboratory Manual," W. H. Freeman C. O., New York, 1990) and in MURRY ("Methods in Molecular Biology," vol.7, Humana Press, Inc., Cliffton, N.J., 1991).

Preferred viruses for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers and microencapsulation.

Examples of inhibitors of Rac1 gene expression include Rac1 siRNA (h): sc-36351 sold by Santa Cruz Biotechnology, inc or siRNA/siAB™ Assay Kit sold by Dharmacon.

The invention further relates to a method for inducing bronchodilation in a patient in need thereof comprising administering a therapeutically effective amount of a Rac1 inhibitor to said patient.

The invention further relates to a method for reducing AHR in a patient in need thereof comprising administering a therapeutically effective amount of a Rac1 inhibitor to said patient.

The inhibitor of the invention may be administered in the form of a pharmaceutical composition, as defined below. Preferably, said inhibitor in a therapeutically effective amount. By a "therapeutically effective amount" is meant a sufficient amount of the agent to treat AHR at a reasonable benefit/risk ratio applicable to any medical treatment.

It will be understood that the total daily usage of the inhibitor of the invention or the pharmaceutical composition comprising thereof will be decided by the attending physician within the scope of sound medical judgment. The specific therapeutically effective dose level for any particular subject will depend upon a variety of factors including the disorder being treated and the severity of the disorder; activity of the specific inhibitor employed; the specific pharmaceutical composition employed, the age, body weight, general health, sex and diet of the subject; the time of administration, route of administration, and rate of excretion of the specific inhibitor employed; the duration of the treatment; drugs used in combination or coincidental with the specific inhibitor employed; and like factors well known in the medical arts. For example, it is well within the skill of the art to start doses of the inhibitor at levels lower than those required to achieve the desired therapeutic effect and to gradually increase the dosage until the desired effect is achieved. However, the daily dosage of the inhibitor may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the agent for the symptomatic adjustment of the dosage to the subject to be treated. A medicament typically contains from about 0.01 mg to about 500 mg of the active ingredient, preferably from 1 mg to about 100 mg of the active ingredient. An effective amount of the active ingredient is ordinarily supplied at a dosage level from 0.0002 mg/kg to about 20 mg/kg of body weight per day, especially from about 0.001 mg/kg to 7 mg/kg of body weight per day.

Any inhibitor of the invention as above described may be combined with pharmaceutically acceptable excipients, and optionally sustained-release matrices, such as biodegradable polymers, to form pharmaceutical compositions.

Pharmaceutical Compositions

Another aspect of the invention thus relates to a pharmaceutical composition comprising a Rac1 inhibitor and a pharmaceutically acceptable carrier for use as bronchodilator in a patient in need thereof.

Still another aspect of the invention relates to a pharmaceutical composition comprising a Rac1 inhibitor and a pharmaceutically acceptable carrier for use in a method for reducing AHR in a subject in need thereof.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions described herein may be in the form suitable for oral administration, for example as a tablet or capsule, for inhalation (including use of dry powder inhalers (DPI), pressurized metered dose inhalers (pMDI) and nebulizers), for parenteral injection (including intravenous, subcutaneous, intramuscular, intravascular or infusion) for example as a sterile solution, suspension or emulsion, for topical administration for example as an ointment or cream, for rectal administration for example as a suppository. In general the pharmaceutical compositions described herein may be prepared in a conventional manner using conventional excipients or carriers that are well known in the art.

Sterile injectable forms of the pharmaceutical compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the agent is combined with emulsifying and suspending agents. If desired, certain sweetening, flavoring or coloring agents may also be added.

The pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

Alternatively, the pharmaceutical compositions are preferably administered to the respiratory tract. Pulmonary delivery compositions can be delivered by inhalation by the subject of a dispersion so that the inhibitor within the dispersion can reach the lung where it can, for example, be readily absorbed through the alveolar region directly into blood circulation. Pulmonary delivery can be achieved by different approaches, including the use of nebulized, aerosolized, micellular and dry powder-based formulations; administration by inhalation may be oral and/or nasal. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. A pharmaceutical composition of the invention may be stably stored as lyophilized or spray-dried powders by itself or in combination with suitable powder carriers. The delivery of a pharmaceutical composition of the invention for inhalation can be mediated by a dosing timing element which can include a timer, a dose counter, time measuring device, or a time indicator which when incorporated into the device enables dose tracking, compliance monitoring, and/or dose triggering to a subject during administration of the aerosol medicament. Examples of pharmaceutical devices for aerosol delivery include metered dose inhalers (MDIs), dry powder inhalers (DPIs), and air-jet nebulizers.

Pharmaceutical compositions of the invention may comprise at least one additional therapeutic agent.

Suitable additional therapeutic agent for use in combination therapy with an inhibitor of the invention is a preferably agent useful in the treatment of respiratory disease.

In one embodiment, said at least one additional therapeutic agent is selected from the group consisting of anti-inflammatory drugs, β2-adrenergic receptor agonists, PDE3, PDE4, mixed PDE3/PDE4 and PDE5 inhibitors and muscarinic M3 antagonists.

Such anti-inflammatory drugs include steroids, for example glucocorticosteroids such as budesonide, fluticasone (e.g. as propionate ester), mometasone (e.g. as furoate ester), beclomethasone (e.g. as 17-propionate or 17,21-dipropionate esters), ciclesonide, ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane,or steroids described in WO 02/88167, WO 02/12266, WO 02/100879, WO 02/00679, WO 03/35668, WO 03/48181, WO 03/62259, WO 03/64445, WO 03/72592, WO 04/39827 and WO 04/66920, and non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248, WO 0505452.

In one particular embodiment, the anti-inflammatory drugs are glucocorticosteroids such as budesonide, fluticasone, mometasone and beclomethasone.

Such β2-adrenergic receptor agonists include short-acting β2 agonists such as salbutamol, terbutaline, metaproterenol, fenoterol and long-acting β2 agonists such as salmeterol, formoterol, bambuterol and clenbuterol.

Such PDE3, PDE4, mixed PDE3/PDE4 and PDE5 inhibitors include roflumilast, cilomilast sildenafil, vardenafil and tadalafil.

Such muscarinic M3 antagonists include aclidinium bromide, tiotropium and ipratropium.

Thus, another aspect of the invention relates to pharmaceutical composition or kit-of-part composition comprising a Rac1 inhibitor and an additional therapeutic agent.

The terms "kit" or "combined preparation", as used herein, define especially a "kit-of-part" in the sense that the combination partners as defined above can be dosed independently or by use of different fixed combinations with distinguished amounts of the combination partners, i.e. simultaneously or at different time points. The parts of the kit-of-part can then, e.g., be administered simultaneously or chronologically staggered, that is at different time points and with equal or different time intervals for any part of the kit-of-part. The ratio of the total amounts of the combination partners to be administered in the combined preparation can be varied. The combination partners can be administered by the same route or by different routes. When the administration is sequential, the first partner may be for instance administered 1, 6, 12, 18 or 24 h before the second partner.

Another aspect of the invention relates to pharmaceutical composition or a kit-of-part composition comprising a Rac1 inhibitor and at least one additional therapeutic agent for use as bronchodilator in a patient in need thereof.

Another aspect of the invention relates to pharmaceutical composition or kit-of-part composition comprising a Rac1 inhibitor and at least one additional therapeutic agent for use in a method for reducing AHR in a subject in need thereof.

The invention will be further illustrated by the following figures and examples. However, these examples and figures should not be interpreted in any way as limiting the scope of the present invention.

FIGURES

FIG. 6: Mice lacking Rac1 in SMC show a decreased airway hyper-responsiveness in asthma. (A) Infiltrating cells in BAL fluid of control and SM-Rac1-KO mice submitted to allergic inflammation protocol with OVA (n=6). (B) Histological grade evaluated on lung sections (n=6). Analysis of airway reactivity to methacholine challenges by (C) non-invasive plethysmography or (D) FlexiVENT approaches in control $Rac1^{lox/lox}$ (n=5–7) and SM-Rac1-KO (n=5–8) mice challenged with OVA. (E) In vivo airway reactivity to methacholine in control naïve mice (ap/ap NaCl) and OVA-challenged mice (o/o NaCl) without and with pre-treatment with salbutamol (ap/ap salbutamol and o/o salbutamol) or Rac1 inhibitor NSC23766 (ap/ap NSC23766 and o/o NSC23766) evaluated by plethysmography (n=9–12). *p<0.05, data are expressed as mean±SEM.

EXAMPLE 1

Rac1 KO Mice in Smooth Muscle Cells and Murine Model of OVA-Induced Asthma

Material & Methods

Mice: All experimental procedures and animal care were performed in accordance with the European Community Standards on the Care and Use of Laboratory Animals and approved by the local ethics committee (Comité d'Ethique en Experiméntation Animale des Pays de Loire). $Rac1^{lox/lox}$ mice were purchased from Jackson Laboratories and SMMHC-$CreER^{T2}$ mice have been reported before. The recombinase Cre was activated in 2 months-old mice by intraperitoneal injection of tamoxifen (T5648, Sigma) for 5 consecutive days during two weeks (1 mg/d dissolved in sun-flower oil). Mice were analyzed 1 month after tamoxifen treatment.

Analysis of Rac1 expression: DNA Rac1 status was performed by amplification of the wild type, floxed and deleted Rac1 alleles using three primers simultaneously. All three primers were included in a single PCR and yielded PCR products of 115 by (wild type), 140 by (Rac deleted), and 242 by (Rac floxed). Detection of Rac1 protein was performed using immunoblots.

Immunoblotting: Cleaned trachea, primary bronchi or aSMC in culture were incubated on ice with lysis buffer supplemented with proteases and phosphatases inhibitors cocktails (Sigma) and sodium orthovanadate. Lysates were subjected to SDS-PAGE, transferred to nitrocellulose membranes and incubated with specific antibodies. Rac1 (610651) was from BD biosciences. MYPT1 (2634), p-Pak (2605), Pak1 (2602) were from Cell Signaling Technology. p-MYPT (sc17556) was from Santa Cruz Biotechnology and tubulin from Beckman Coulter. Immune complexes were detected with appropriate secondary antibodies and enhanced chemiluminescence reagent (ECL plus, GE Healthcare). Protein band intensities were quantified using ImageJ Software (NIH software).

Histological analysis: Lungs were fixed in 4% paraformaldehyde in PBS and embedded into paraffin. 6 μm sections were stained with hematoxylin and eosin (Sigma). Histological grade was determined to assess inflammation.

Respiratory parameters: Physiocages (Bioseb) were used to measure gaz exchanges during 24 h after a two-day acclimatizing period. The recording room was maintained with a 12-hour-light/12-hour-dark cycle.

Analysis of airways reactivity ex vivo: Primary bronchi were cut in 2 mm-long rings and mounted on a multichannel isometric myograph (Danish Myo Technology) containing a Krebs-Henseleit solution (118.4 mM NaCl, 4.7 mM KCl, 2 mM CaCl2, 1.2 mM MgSO4, 1.2 mM KH2PO4, 25 mM NaHCO3 and 11 mM glucose). A pre-tension of 0.5 mN was applied and maintained all along the protocol. We constructed cumulative concentration-response curves in response to KCl and methacholine (Sigma). When indicated, we pretreated rings with EHT1864 (Sigma) or NSC23766 (Calbiochem) Rac1 inhibitors at 10 μM, 1 h before contraction. Chambers wire myograph were connected to a digital data recorder (MacLab/4e, AD Instruments) and recordings were analyzed using LabChart v7 software (AD Instruments).

Analysis of airways responsiveness in vivo: Airway responsiveness was assessed in conscious, unrestrained mice using a barometric, whole-body plethysmography (EMKA Technologies) by recording respiratory pressure curves in response to inhaled methacholine (Sigma) at concentrations of 0-40 mg/ml for 1 min. Airway responsiveness was expressed in enhanced pause (Penh) units. The Penh values measured after stimulation were averaged and expressed as the fold-increase over baseline values. Alternatively, dynamic airway resistance was measured using a Flexivent® apparatus (SCIREQ). In this case, mice were anesthetized by a ketamine/xylazine solution, tracheotomized, paralyzed and immediately intubated, followed by mechanical ventilation. Respiratory frequency was set at 150 breaths/min. Increasing concentrations of methacholine (0-15 mg/mL) were administered via a nebulizer aerosol system (Aeroneb, Aerogen). When required, Rac inhibitor NSC23766 and salbutamol were nebulized (300 µl at indicated concentration) 10 min before methacholine challenge.

Allergic asthma induction: When indicated, asthma was induced in mice by intraperitoneal injections with ovalbumin (OVA) in alum (Sigma) at D0, D14 and D21. Mice were challenged at D27, D28 and D29 through intranasal route with aerosolized OVA (50 µg in phosphate-buffered saline). These OVA-sensitized mice were used as a model of in vivo chronic asthma. Control mice were sensitized with PBS/alum and then were challenged with PBS.

Bronchoalveolar lavage analysis: Mice were tracheotomized and 1 ml of sterile PBS was administrated intratracheally through a catheter. Cells and supernatants from recovered fluid were separated by centrifugation. Total cell number was determined by optical microscopy.

Cell culture: Primary airway smooth muscle cells were isolated from trachea and primary bronchi of the indicated mouse strain. Tissues were cleaned manually and the muscular layer was further digested 1 h with collagenase II (1 mg/mL, Worthington) at 37° C. under agitation. Cells grew up in DMEM (Gibco; Invitrogen) containing 15% fetal bovine serum, 100 units/mL penicillin and 100 µg/mL streptomycin at 37° C. and 5% CO2. The culture medium was changed every 72 hours. All experiments were performed between passages 1 and 2.

Intracellular calcium measurements: $Rac1^{lox/lox}$ and $SM\text{-}Rac1^{lox/lox}$ cells were seeded in 8-chamber borosilicate coverglass (Lab-Tek) and treated with 4-hydroxy-tamoxifen (1 µM, 48 h) to induce Rac1 deletion in SM-Cre positive cells. FluoForte probes were loaded using FluoForte calcium assay kit (Enzo Life Science) according to the supplier's specifications. When indicated, 10 µM of Rac1 inhibitors were added 1 h before loading probes. After basal fluorescence recording, cells were stimulated with KCl (100 mM) or carbachol (30 µM). The fluorescence was recorded using Metamorph software and quantified with ImageJ Software (NIH software).

Statistics: All data are expressed as the mean±SEM of sample size n. For multiple comparisons, one-way ANOVA was used, followed by Bonferroni's test. For individual comparisons, statistical analysis was performed using Student's t-test. Data analysis was performed using the GraphPad Prism software. The threshold for statistical significance was set at $p<0.05$.

Results

Figure 1:
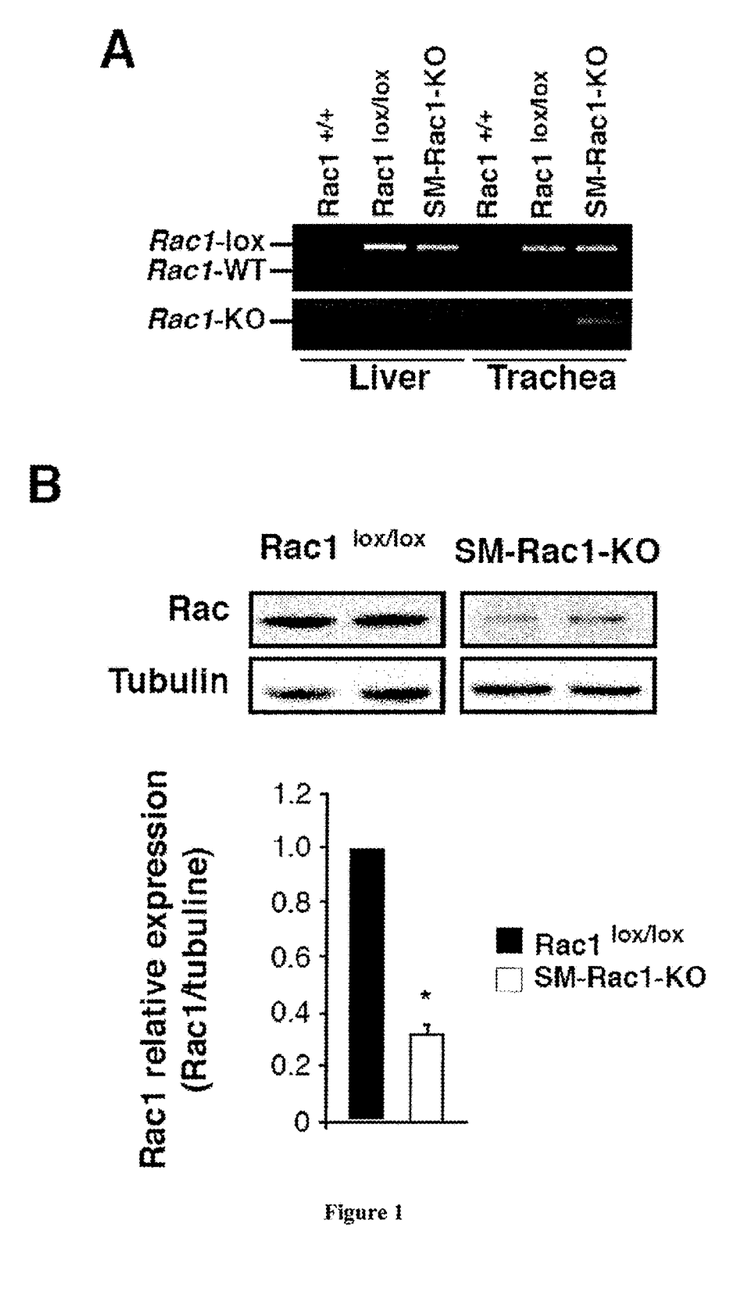
FIG. 1: Validation of Rac1 deletion in SMC. (A) Genomic DNA status detected by PCR and (B) immunoblot analysis of Rac1 protein expression in tracheas from the indicated mice after tamoxifen treatment (n=4) *p<0.05, data are expressed as mean±SEM.

Generation of mice with smooth muscle-specific Rac1 deficiency: To investigate in vivo the role of Rac1 in airway smooth muscle cells (aSMC), we generated mice lacking Rac1 specifically in SMC (SM-Rac1-KO mice). We mated transgenic mouse line with floxed alleles of the gene coding for Rac1 ($Rac1^{lox/lox}$) to mice expressing a fusion protein of the Cre recombinase with the modified oestrogen receptor-binding domain ($CreER^{T2}$) under the control of the smooth muscle myosin heavy chain (SMMHC) promoter (SMMHC $CreER^{T2}$ mice) to produce SMMHC-$CreER^{T2}$; $Rac1^{lox/lox}$ mice (SM-$Rac1^{lox/lox}$ mice). SM-Rac1-KO mice were then obtained by treating SM-$Rac1^{lox/lox}$ mice with tamoxifen. Wild type and floxed Rac1 alleles could be easily identified by PCR (WT, 115 bp; $Rac1^{lox/lox}$ 242 bp). SM-Rac1-KO mice were characterized by the appearance of a 140 by band resulting from the Cre-mediated deletion of the floxed Rac1 alleles in tamoxifen-treated SM-$Rac1^{lox/lox}$ mice (FIG. 1, A). Deletion of Rac1 in aSMC was confirmed by western-blot analysis showing that Rac1 protein was poorly detected in trachea and bronchi (FIG. 1, B).

Figure 2:
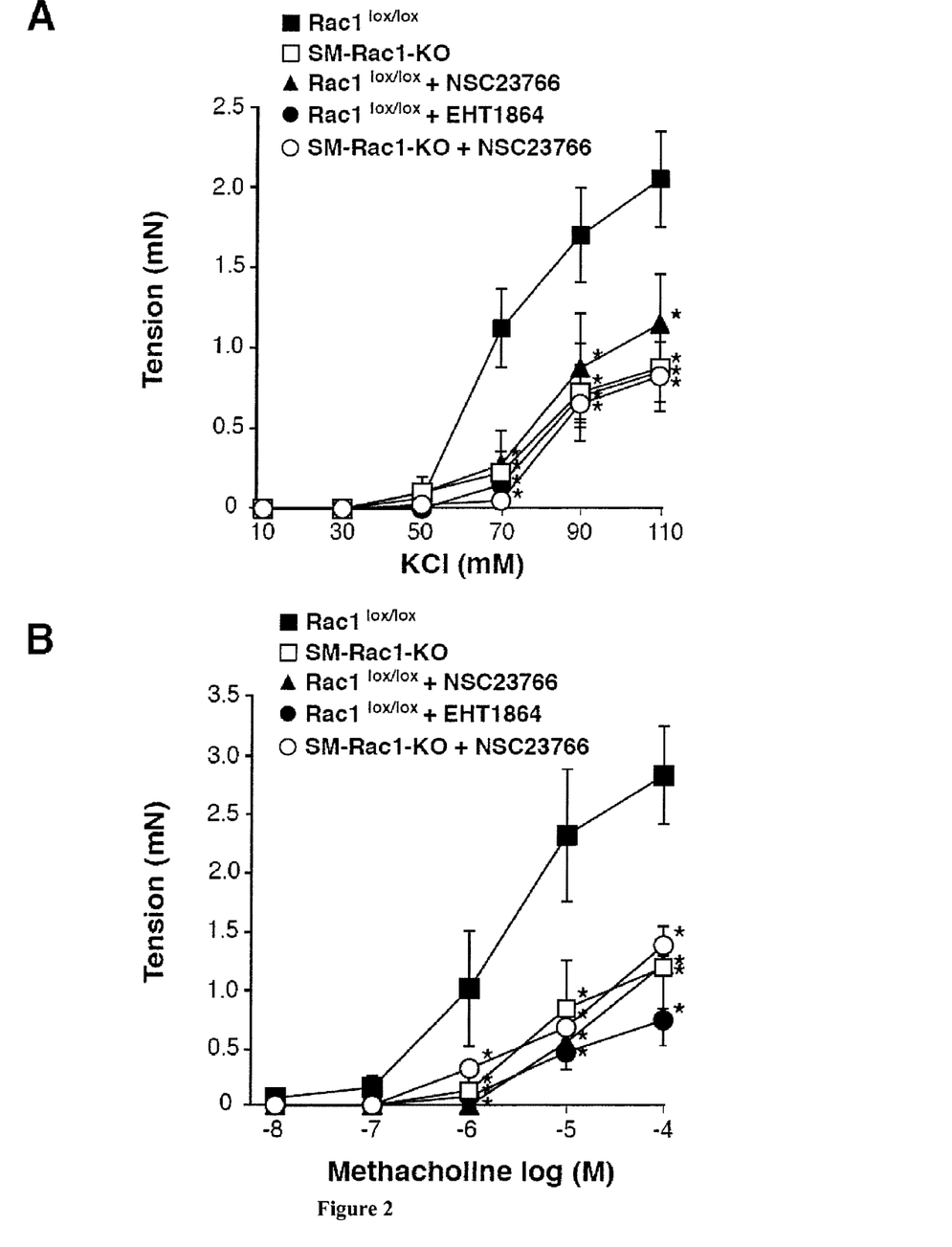
FIG. 2: Contractile properties of SM-Rac1-KO bronchi. Contractile responses to (A) KCl (n=5–7) and (B) methacholine (n=5–7) in bronchi from control and SM-Rac1-KO mice. When indicated, bronchial rings were pre-treated with Rac1 inhibitors (NSC23766 or EHT1864) (n=4–5). Log M, logarithm of the molar concentration used for each agent. *p<0.05 compared with controls. Data are expressed as mean±SEM.

Inhibition of Rac1 prevents bronchoconstriction in mice: To investigate the role of Rac1 in aSMC, we determined the contractile response of SM-Rac1-KO bronchi to methacholine, an agonist of muscarinic receptors, or KCl. The maximal contractions induced by both KCl (FIG. 2, A) and methacholine (FIG. 2, B) were reduced by ~50% in bronchial rings from SM-Rac1-KO mice compared to control mice. To confirm a direct role of Rac1 activity in the regulation of bronchoconstriction, we analyzed the effect of two types of Rac1 inhibitors (NSC23766 and EHT1864) on the contractile responses to methacholine or KCl in bronchial rings from control $Rac^{lox/lox}$ mice. In the presence of NSC23766 (10 µM) or EHT1864 (10 µM), the concentration-response curves to methacholine or KCl in $Rac^{lox/lox}$ bronchial rings were similar to those recorded in non-treated bronchial rings from SM-Rac1-KO mice. Moreover, the absence of any effect of NSC23766 on KCl- and methacholine-induced contraction of bronchial rings from SM-Rac1-KO mice (FIG. 2, A and B) attested that the action of Rac1 inhibitors on the contraction of control bronchial rings resulted from a specific action on smooth muscle Rac1. All these data indicated that aSMC Rac1 contributes to bronchial contractile response.

Figure 3:
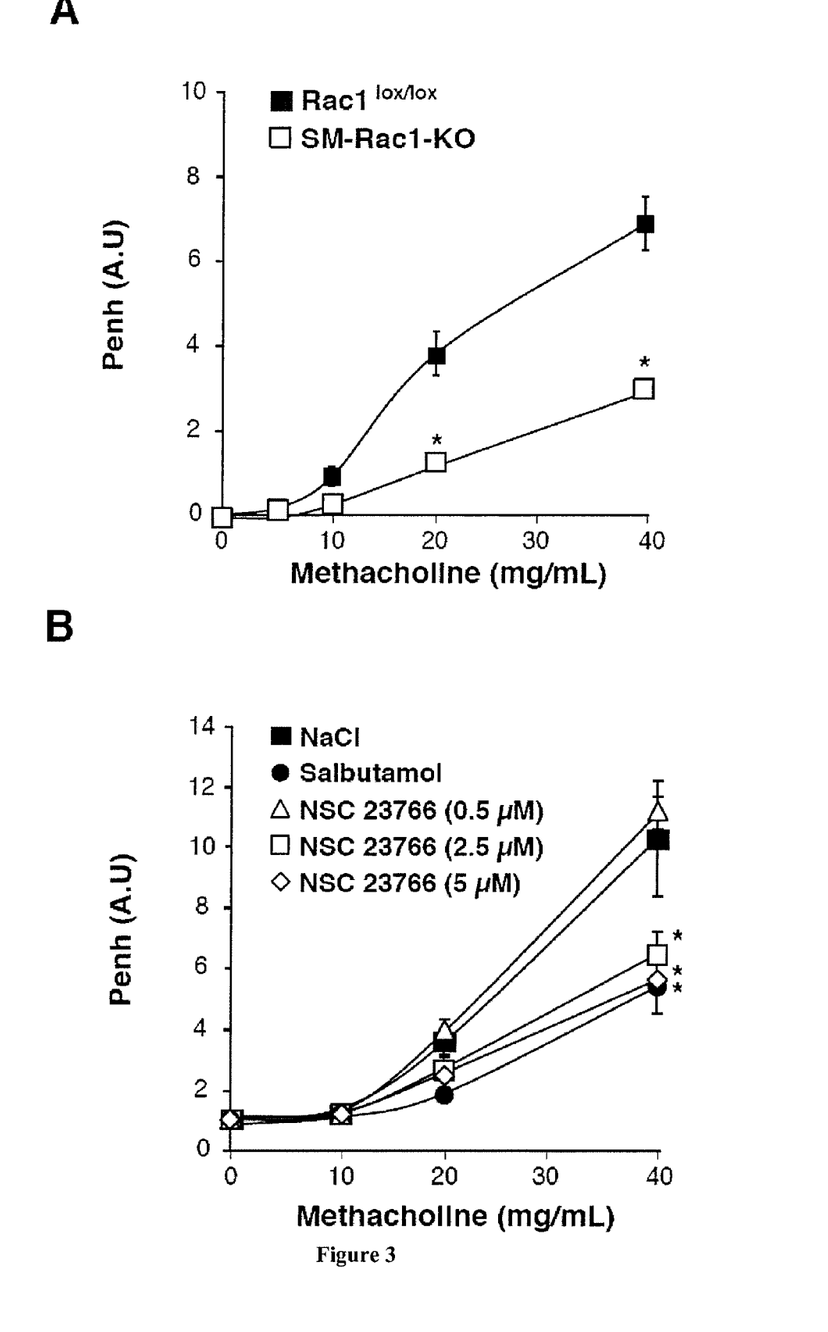
FIG. 3: Rac1 deficiency in aSMC prevents methacholine-induced airways contraction. In vivo analysis of airways reactivity to methacholine by a non-invasive plethysmography approach (A) in SM-Rac1-KO (n=12) or control mice (n=12), (B) treated or not with NSC23766 (n=10) or salbutamol (n=10). A.U, arbitrary units. *p<0.05 compared with controls. Data are expressed as mean±SEM.

To confirm in vivo the role of Rac1 in bronchoconstriction, pulmonary function was monitored in mice by a non-invasive plethysmography approach. In vivo bronchoconstriction induced by increasing doses of methacholine is considerably attenuated in SM-Rac1-KO mice (FIG. 3, A). Moreover, nebulization of the Rac inhibitor NSC23766 prevented methacholine-dependent bronchoconstriction (FIG. 3, B) in a dose-dependent manner in control mice. Interestingly, that efficiency of NSC23766 aerosol inhalation is similar to that of salbutamol (FIG. 3, B), a reference short-acting β2-agonist bronchodilator used in asthma and chronic obstructive pulmonary disease (COPD). These results attest that Rac1 in aSMC is involved in signaling pathways leading to bronchoconstriction.

Figure 4:
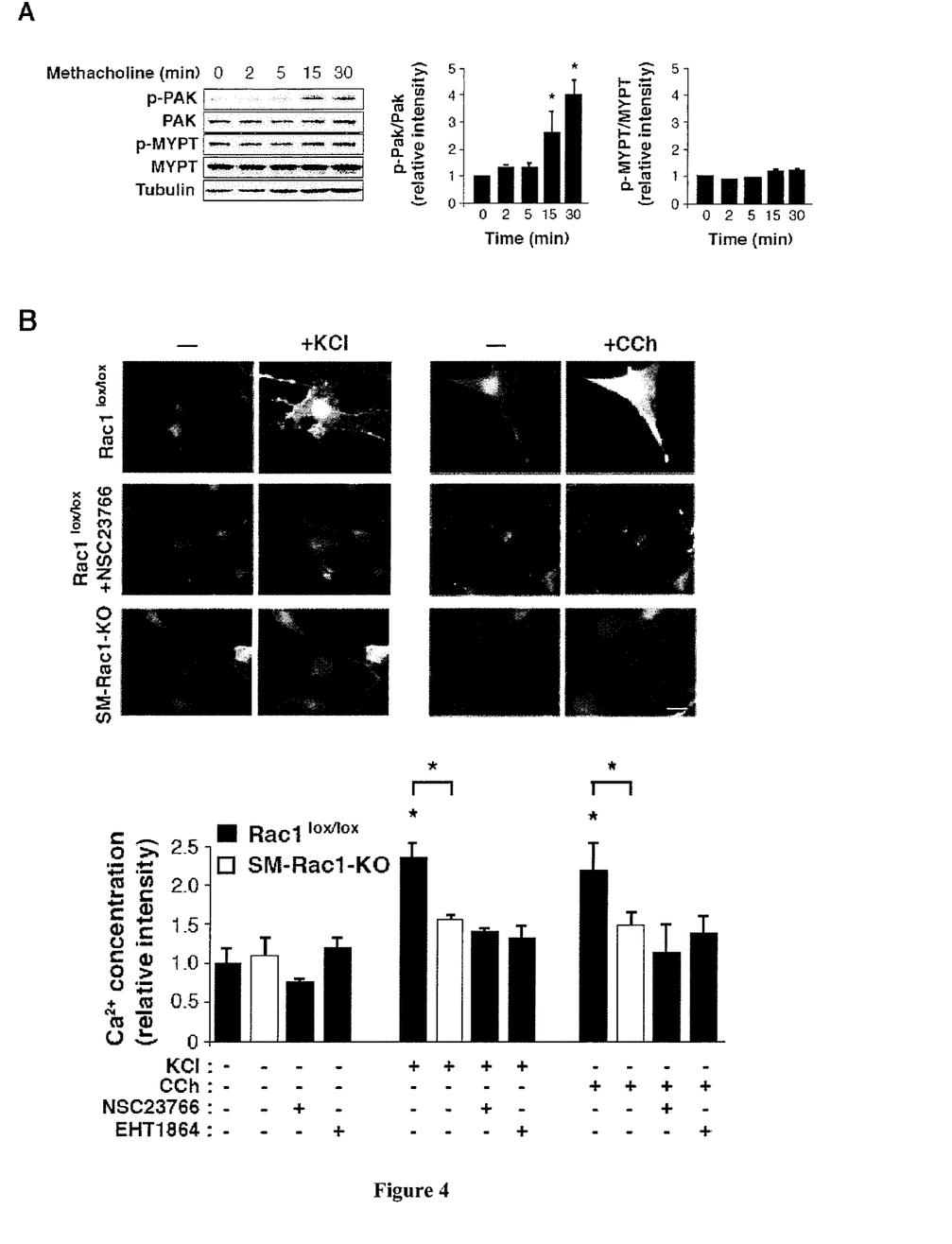
FIG. 4: Inhibition of Rac1 in aSMC impairs intracellular $Ca^{2+}$ increase during agonist stimulation. (A) Immunoblot analysis of Pak1, MYPT and $MLC_{20}$ phosphorylation in aSMC during methacholine stimulation (n=3). (B) Representative images of intracellular calcium levels in $Rac1^{lox/lox}$ and Rac1-deleted aSMC loaded with Fluoforte probe, scale bar 20 μm. Cells were pre-incubated 1 h with Rac1 inhibitors (NSC23766 or EHT 1864) when indicated and stimulated with potassium chloride (KCl) or carbachol (Cch). For each condition, pick of calcium were quantified in 25 cells. Data are expressed as mean±SEM, *p<0.05.

Rac1 participates to the increase of intracellular $Ca^{2+}$ concentration during aSMC contraction: Phosphorylation of the 20 kDa myosin light chain ($MLC_{20}$) is an essential factor that promotes SMC contraction. $MLC_{20}$ phosphorylation is controlled by the activity of two enzymes: the $Ca^{2+}$-calmodulin-activated MLC kinase (MLCK), activated by a rise in cytosolic $Ca^{2+}$ concentration, and the $Ca^{2+}$-independent MLC phosphatase (MLCP). Phosphorylation of the regulatory subunit of MLCP, MYPT, inhibits the enzymatic activity of MLCP, thus promoting increased $MLC_{20}$ phosphorylation and contraction. Most of endogenous contractile agonists induce contraction by increasing both (i) the cytosolic $Ca^{2+}$ concentration and MLCK activity, and (ii) the phosphorylation of MYPT and inhibition of MLCP. During methacholine stimulation of aSMC in culture, we observed an increase of phosphorylation of the Rac1 downstream effector, Pak1 (FIG. 4, A). However, no modification of p-MYPT was detected, suggesting that the contraction induced by methacholine was dependent of Rac1/Pak1 signaling pathway but independent of p-MYPT-mediated regulation of MLCP. Therefore, we analyzed the role of Rac1 on bronchoconstrictor-induced increase in cytosolic $Ca^{2+}$ in aSMC. As expected, the muscarinic cholinergic receptor agonist carbachol and KCl induced a rise of $Ca^{2+}$ in control aSMC, which was significantly smaller in aSMC from SM-Rac1-KO mice (FIG. 4B). A similar reduction of the $Ca^{2+}$ rise was observed in WT aSMC treated with Rac1 inhibitors (FIG. 4, B). This alteration of the $Ca^{2+}$ signaling in SM-Rac1-KO aSMC suggests that Rac1 activity controls aSMC contraction by participating to the mechanisms responsible for the rise in intracellular $Ca^{2+}$ induced by bronchoconstrictors.

Figure 5:
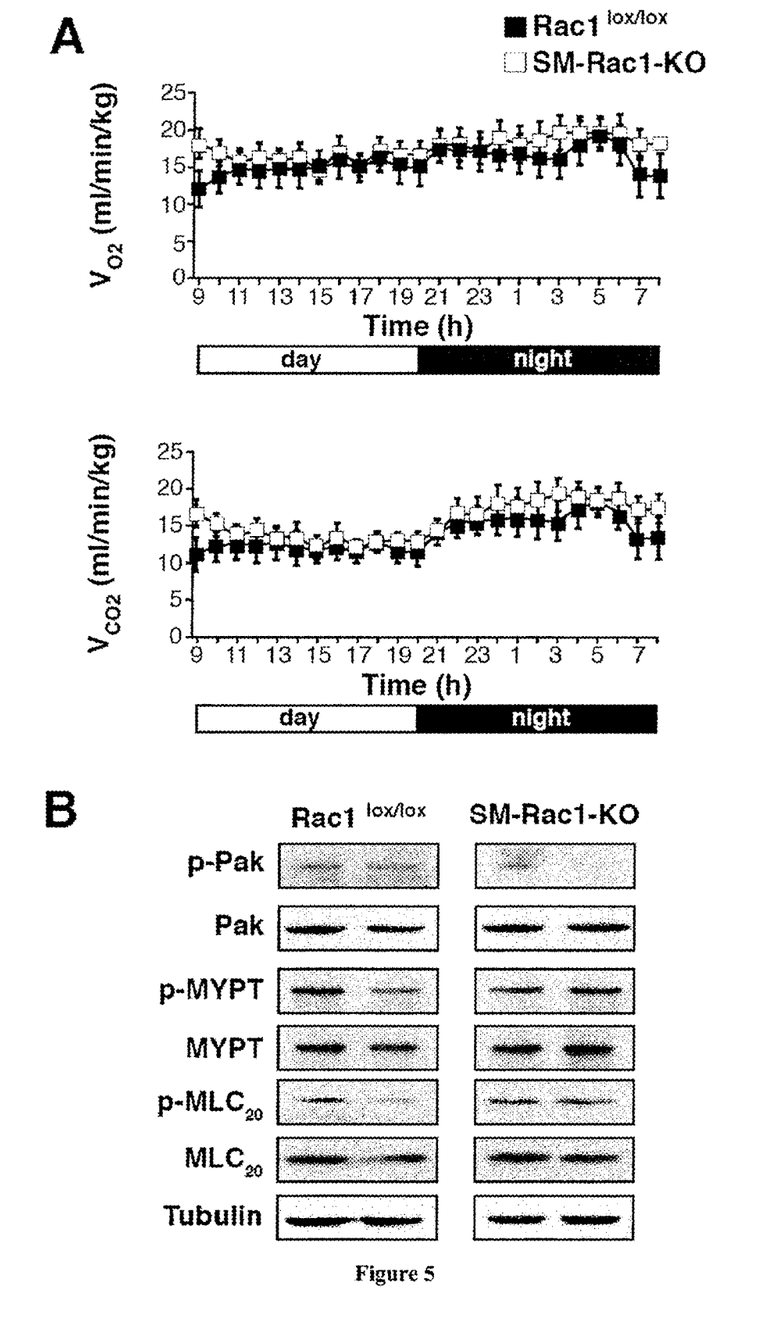
FIG. 5: Analysis of respiratory parameters in SM-Rac1-KO mice. (A) Respiratory function measured in metabolic cages to assess gaz exchanges in $Rac1^{lox/lox}$ (n=6) and SM-Rac1-KO mice (n=6). (B) Immunoblot analysis of contractile proteins expression in $Rac1^{lox/lox}$ and SM-Rac1-KO tracheas (n=4). *p<0.05, data are expressed as mean±SEM.

Inhibition of Rac1 protects from airway hyper-responsiveness: Then, the impact of SM Rac1 deletion on respiratory system was evaluated by a comprehensive examination of SM-Rac1-KO mice at histological and physiological levels. The evaluation of respiratory metabolism revealed that oxygen consumption ($V_{O2}$), dioxide production ($V_{CO2}$) and respiratory exchange rate are similar in both group of mice during both 12-h dark and 12-h light periods (FIG. 5, A). In addition, we analyzed the contraction status of aSMC in these mice. Consistent with our in vitro results, same level of $p-MLC_{20}$ and p-MLCP are detected in bronchi from control and SM-Rac1-KO mice under basal condition (FIG. 5, B). This data thus show that SM-Rac1 deletion does not alter lung function under resting physiological condition, when airways are not or weakly contracted.

Therefore we hypothesized that Rac1 could be engaged in respiratory diseases characterized by airway hyper-responsiveness (AHR) and bronchial narrowing. To assess this hypothesis, we analyzed the role of Rac1 in aSMC in allergic airway model. Respiratory challenge with ovalbumin (OVA) in mice previously sensitized to OVA intra-peritoneally induces alterations similar to those seen in human allergic asthma, including AHR and airway inflammation. In OVA-sensitized control and SM-Rac1-KO mice, we detected similar number of cells in bronchoalveolar lavage fluid (FIG. 6, A) and a comparable grade of pulmonary inflammation (FIG. 6, B), indicating that losing Rac1 expression in aSMC did not influence the adaptive immune response to ovalbumin.

Figure 6:
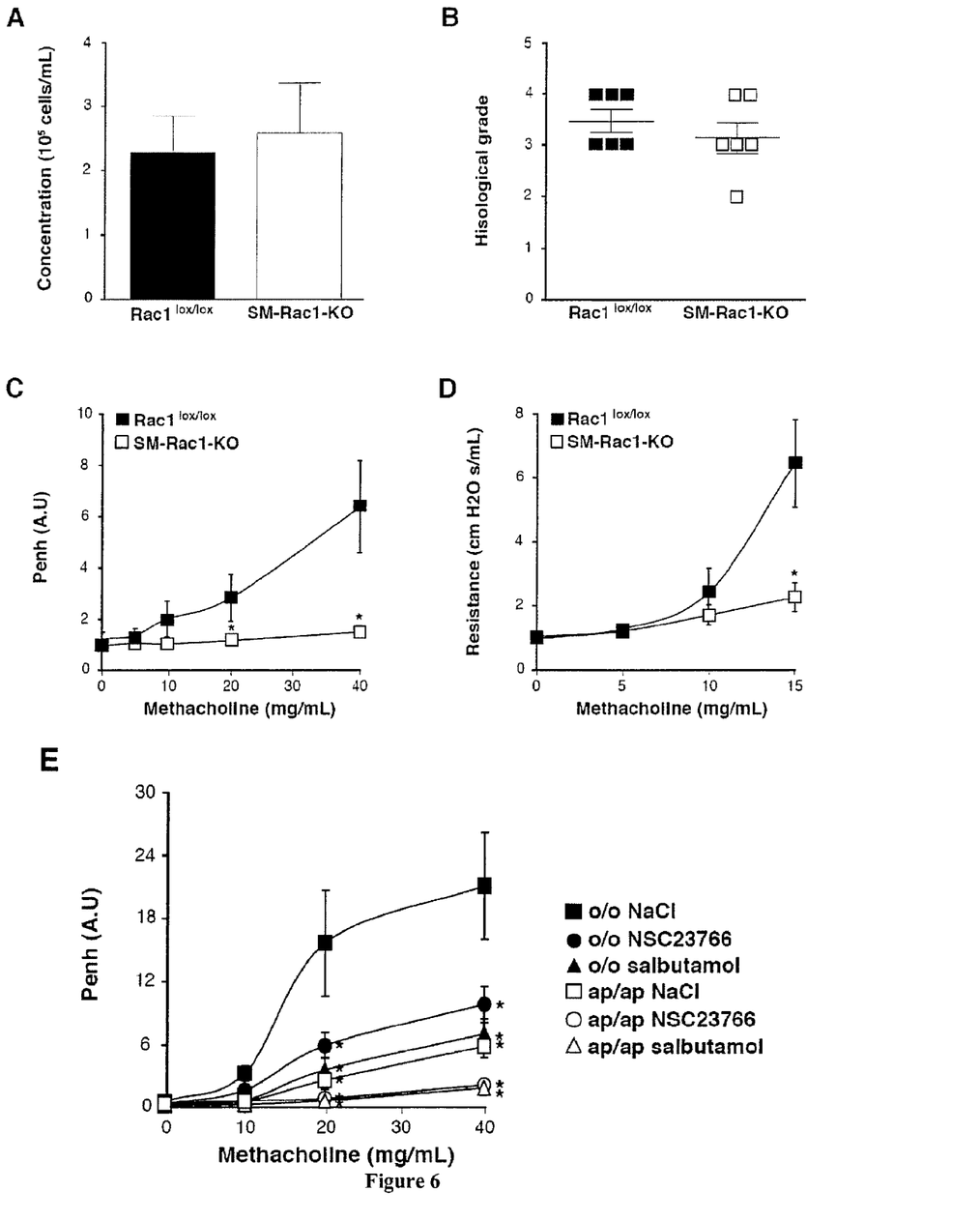

The assessment of airway function by barometric whole-body plethysmography revealed that sensitized and challenged control $Rac1^{lox/lox}$ mice had significantly increased airway reactivity to methacholine while this AHR was not recorded in SM-Rac1-KO mice (FIG. 6, C). To complement this observation, pulmonary resistance was analyzed in anesthetized, tracheotomized, and ventilated mice. This study confirmed that OVA-sensitized $Rac1^{lox/lox}$ mice showed significantly higher pulmonary resistance in response to methacholine than Rac1-KO mice (FIG. 6, D). These results indicated that despite a normal inflammatory response induced by OVA, SM-Rac1-KO mice are resistant to AHR induced in the OVA model of asthma.

To evaluate the role of Rac activity in AHR in asthma, NSC23766 was nebulized before methacholine challenge in naive and OVA-sensitized control mice. The pharmacological inhibition of Rac1 almost completely prevented the AHR to methacholine in the OVA model of asthma (FIG. 6, E, o/o NaCl compared to o/o NSC23766). The effect of NSC23766 aerosol inhalation was comparable to that of salbutamol treatment in both naïve (FIG. 6, E; ap/ap NaCl compared to ap/ap NSC23766 and ap/ap salbutamol) and OVA-sensitized mice (FIG. 6, E; o/o NaCl compared to o/o NSC23766 and o/o salbutamol).

EXAMPLE 2

Murine Model of Experimental House Dust Mite-Induced Asthma

Material & Methods

Allergic asthma induction: House dust mite model (HDM) of chronic asthma was used. In this case, mice were sensitized on days D0, D7, D14 and D21 by skin application of 500 µg of total extract of HDM Der f (Stallergenes) in 20 µL of dimethylsulfoxyde (DMSO, Sigma-Aldrich) on the ears. DMSO was used as an irritant able to facilitate the allergen penetration. Intranasal challenges were performed with Der f (250 µg in phosphate-buffered saline 250) on D27 and D34. Mice were sacrificed on D35 for ex vivo analysis.

Results

Figure 7:
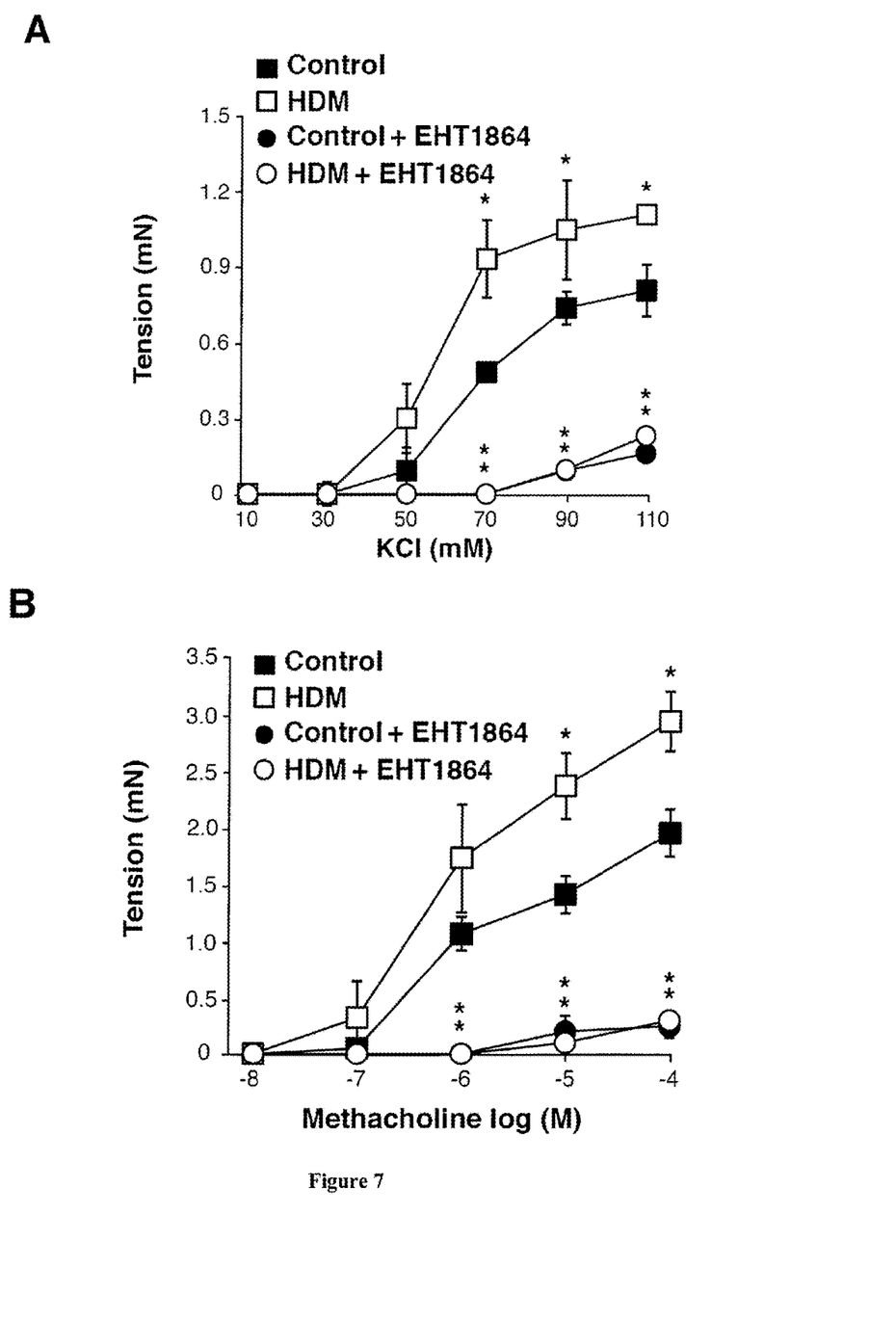
FIG. 7: Rac1 inhibition prevents methacholine-induced hyperresponsiveness observed in bronchi of asthmatic mice ex vivo. Contractile responses to (A) KCl and (B) methacholine (n=2) in bronchi from control and house dust mite-sensitized mice. When indicated, bronchial rings were pre-treated with the Rac1 inhibitor EHT1864. Log M, logarithm of the molar concentration used for methacholine. *p<0.05 compared with controls. Data are expressed as mean±SEM.

To confirm the direct role of Rac1 activity in AHR, we analyzed the effect of EHT1864 on the contractile responses to methacholine and KCl in bronchial rings from control and house dust mite (HDM)-sensitized mice (FIG. 7). We recorded in this allergic animal model a stronger contraction in response to KCl (FIG. 7, A) and methacholine (FIG. 7, B) compared to control animals, attesting AHR in HDM sensitized-mice. In presence of Rac inhibitor, methacholine and KCl contractions are inhibited in both group of bronchial rings. After EHT1864 treatment, bronchial reactivities of control and HDM sensitized-mice are similar.

All these results suggest that Rac1 plays a major role in the contraction of aSMC and AHR in asthma and that aerosol inhalation of Rac1 inhibitors could be a new strategy to induce bronchodilation in asthma and COPD.

The invention claimed is:
1. A method for inducing bronchodilation in a patient in need thereof, comprising
  administering to the patient a therapeutically effective amount of a Rac1 inhibitor, wherein said step of administering results in bronchodilation in the patient, and wherein said patient suffers from an airway disease in which airway inflammation is not involved.
2. The method according to claim 1, wherein the patient in need thereof suffers from exercise-induced asthma in which airway inflammation is not involved.
3. The method according to claim 1, wherein the patient in need thereof is a salbutamol-resistant patient.
4. The method according to claim 1, wherein the patient suffers from a bronchoconstructive disorder which is not caused by airway inflammation.

* * * * *